(12) United States Patent
Greene et al.

(10) Patent No.: US 8,133,206 B2
(45) Date of Patent: *Mar. 13, 2012

(54) SAFETY INTRAVENOUS CATHETER ASSEMBLY

(75) Inventors: Elliott S. Greene, Altamont, NY (US); Jason A. Greene, Wynnewood, PA (US)

(73) Assignee: Albany Medical College, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/511,706

(22) Filed: Jul. 29, 2009

(65) Prior Publication Data

US 2009/0292261 A1   Nov. 26, 2009

Related U.S. Application Data

(63) Continuation of application No. 10/961,832, filed on Oct. 8, 2004, now Pat. No. 7,569,033, which is a continuation of application No. PCT/US03/10756, filed on Apr. 9, 2003, which is a continuation of application No. 10/120,005, filed on Apr. 10, 2002, now Pat. No. 6,689,102, which is a continuation-in-part of application No. 09/840,699, filed on Apr. 23, 2001, now Pat. No. 6,695,814, which is a continuation of application No. 09/127,374, filed on Jul. 31, 1998, now Pat. No. 6,221,047.

(51) Int. Cl.
*A61M 5/178* (2006.01)

(52) U.S. Cl. ......... 604/164.08; 604/164.07; 604/164.01; 604/198; 604/263

(58) Field of Classification Search ............... 604/93.01, 604/110, 162, 164.01–164.09, 164.11, 165.01, 604/165.02, 181–182, 187–188, 198, 209–211, 604/263–264, 272, 523, 164.1, 164.12, 164.13, 604/165.03, 166.01–170.03

See application file for complete search history.

(56) References Cited

U.S. PATENT DOCUMENTS 4,944,725 A * 7/1990 McDonald ............... 604/164.08

(Continued)

FOREIGN PATENT DOCUMENTS

WO    WO 90/08564    8/1990

(Continued)

OTHER PUBLICATIONS

Decision on Petition of the United States Patent and Trademark Office dated Sep. 28, 2008, granting amendment to claim of priority regarding International Patent Application, Serial No. PCT/US2003/10756.

(Continued)

*Primary Examiner* — Quynh-Nhu H Vu
(74) *Attorney, Agent, or Firm* — Heslin Rothenberg Farley & Mesiti P.C.

(57) ABSTRACT

A safety intravenous catheter assembly includes a needle, a catheter hub having an axial bore extending through the catheter hub and a notch extending outwardly in the axial bore, a needle cover, and a notch clip connected to the needle cover. The notch clip is selectively maintained adjacent the needle throughout a range of positions from being in forceful contact with the needle to being generally spaced from the needle and selectively maintained adjacent the catheter hub throughout a range of positions from being in forceful contact with the catheter hub to being generally spaced from the catheter hub to lock the catheter hub to the needle cover while being operable to move the needle relative to the notch clip in a near frictionless relationship.

11 Claims, 8 Drawing Sheets

U.S. PATENT DOCUMENTS

| | | | | |
|---|---|---|---|---|
| 4,952,207 | A | 8/1990 | Lemieux | 604/164 |
| 4,964,854 | A | 10/1990 | Luther | 604/166 |
| 4,978,344 | A | 12/1990 | Dombrowski et al. | 604/198 |
| 5,019,049 | A * | 5/1991 | Haining | 604/165.02 |
| 5,102,394 | A * | 4/1992 | Lasaitis et al. | 604/164.08 |
| 5,135,504 | A | 8/1992 | McLees | 604/164 |
| 5,215,525 | A | 6/1993 | Sturman | 604/164 |
| 5,300,045 | A * | 4/1994 | Plassche, Jr. | 604/263 |
| 5,322,517 | A | 6/1994 | Sircom et al. | |
| 5,366,447 | A | 11/1994 | Gurley | 604/192 |
| 5,419,766 | A | 5/1995 | Chang et al. | 604/110 |
| 5,458,658 | A * | 10/1995 | Sircom | 604/192 |
| 5,549,558 | A * | 8/1996 | Martin | 604/110 |
| 5,558,651 | A | 9/1996 | Crawford et al. | 604/263 |
| 5,599,310 | A | 2/1997 | Bogert | 604/164 |
| 5,688,249 | A | 11/1997 | Chang et al. | 604/198 |
| 5,700,250 | A | 12/1997 | Erskine | 604/263 |
| 5,769,827 | A * | 6/1998 | DeMichele et al. | 604/263 |
| 5,830,189 | A | 11/1998 | Chang | |
| 5,910,132 | A | 6/1999 | Schultz | 604/162 |
| 5,935,109 | A | 8/1999 | Donnan | 604/164 |
| 5,935,110 | A | 8/1999 | Brimhall | 604/167 |
| 5,951,515 | A | 9/1999 | Osterlind | 604/110 |
| 6,117,108 | A | 9/2000 | Woehr et al. | 604/110 |
| 6,156,015 | A * | 12/2000 | DeMichele et al. | 604/263 |
| 6,221,047 | B1 * | 4/2001 | Greene et al. | 604/164.01 |
| 6,689,102 | B2 * | 2/2004 | Greene | 604/164.08 |
| 6,695,814 | B2 * | 2/2004 | Greene et al. | 604/164.08 |
| 7,569,033 | B2 * | 8/2009 | Greene et al. | 604/164.08 |

FOREIGN PATENT DOCUMENTS

WO     WO 03/086499     10/2003

OTHER PUBLICATIONS

Office Action dated Mar. 25, 2011, issued in Reexamination of U.S. Patent No. 7,569,033, Reexamination U.S. Appl. No. 90/011,354, 13-pages.

* cited by examiner

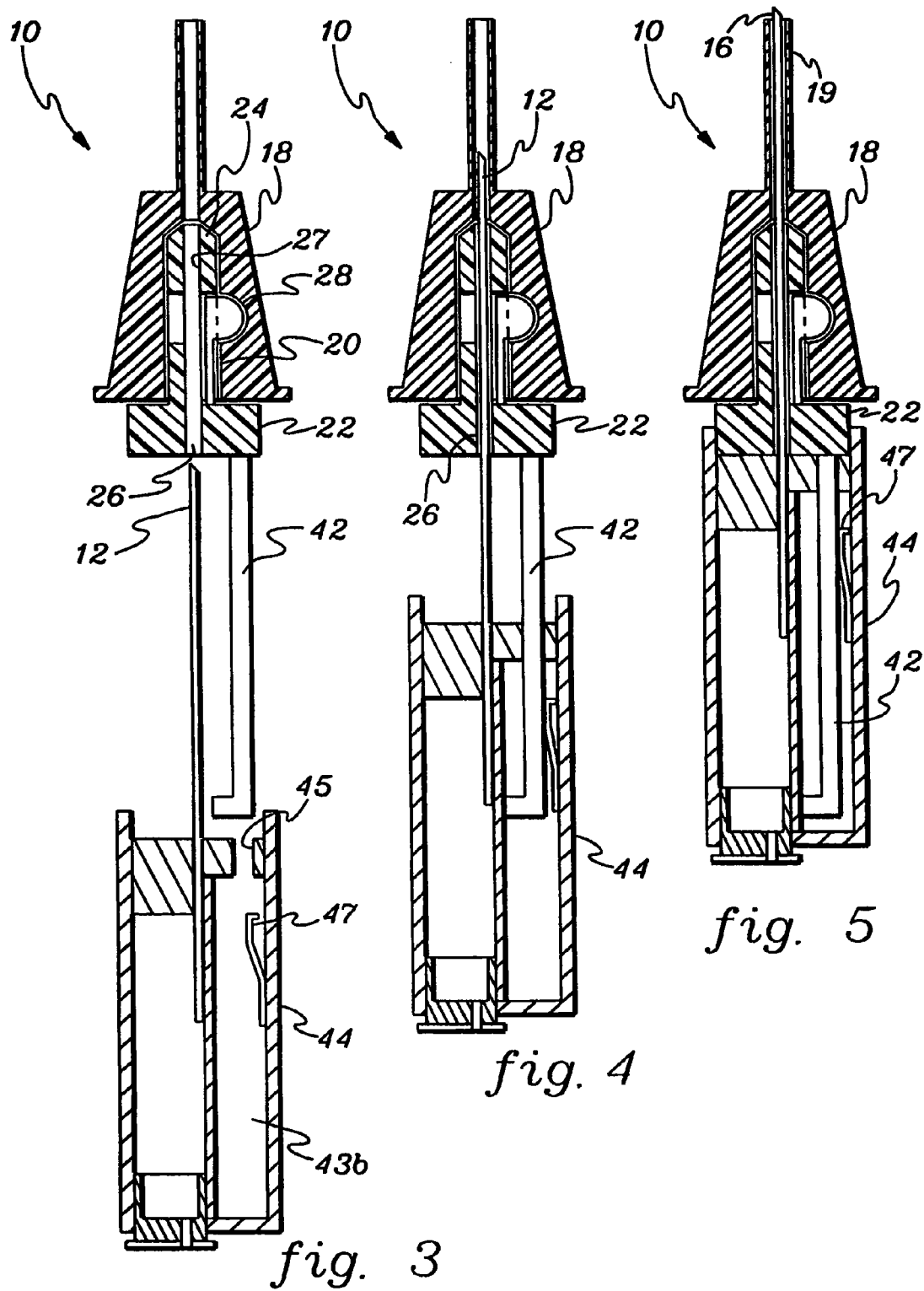

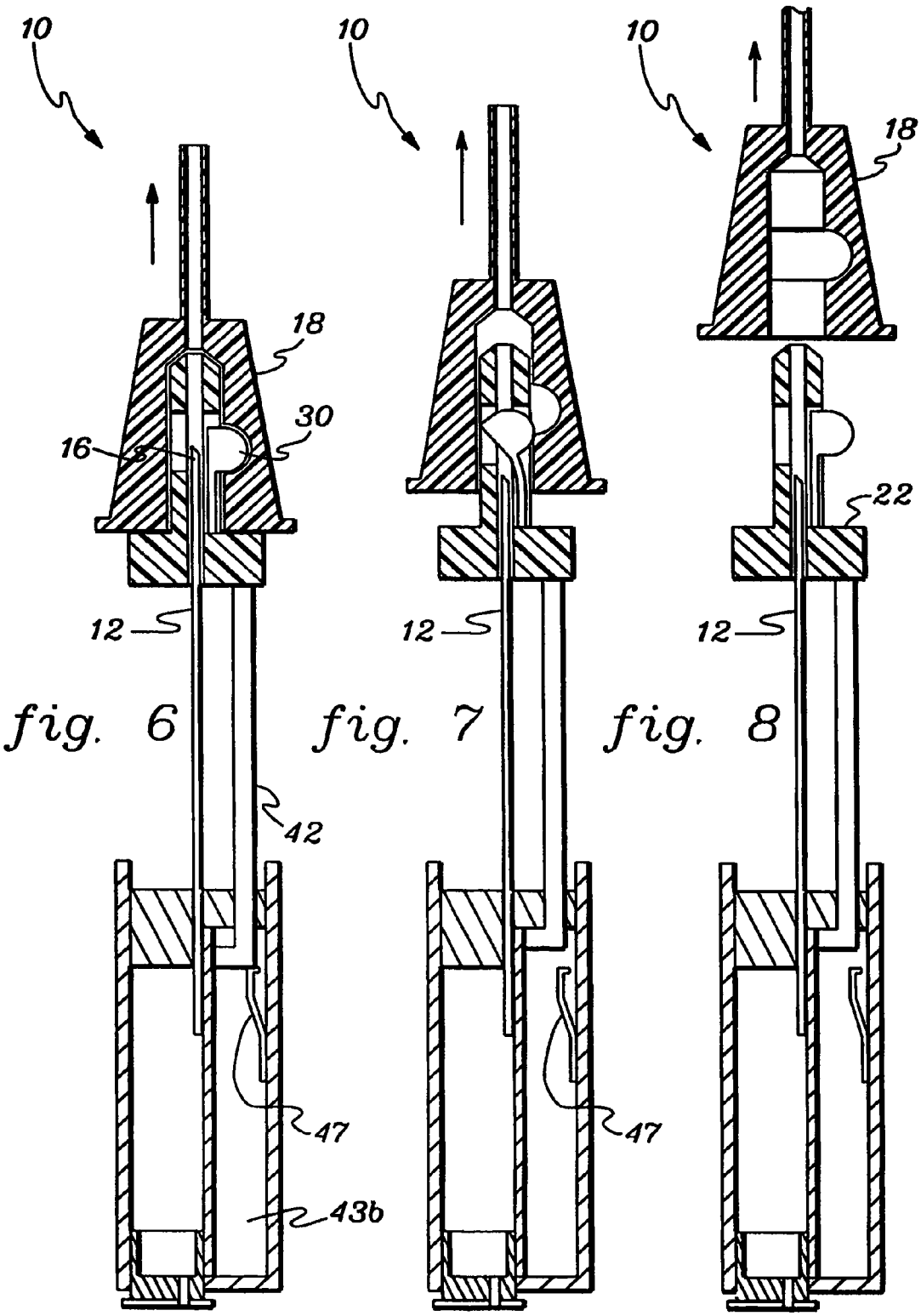

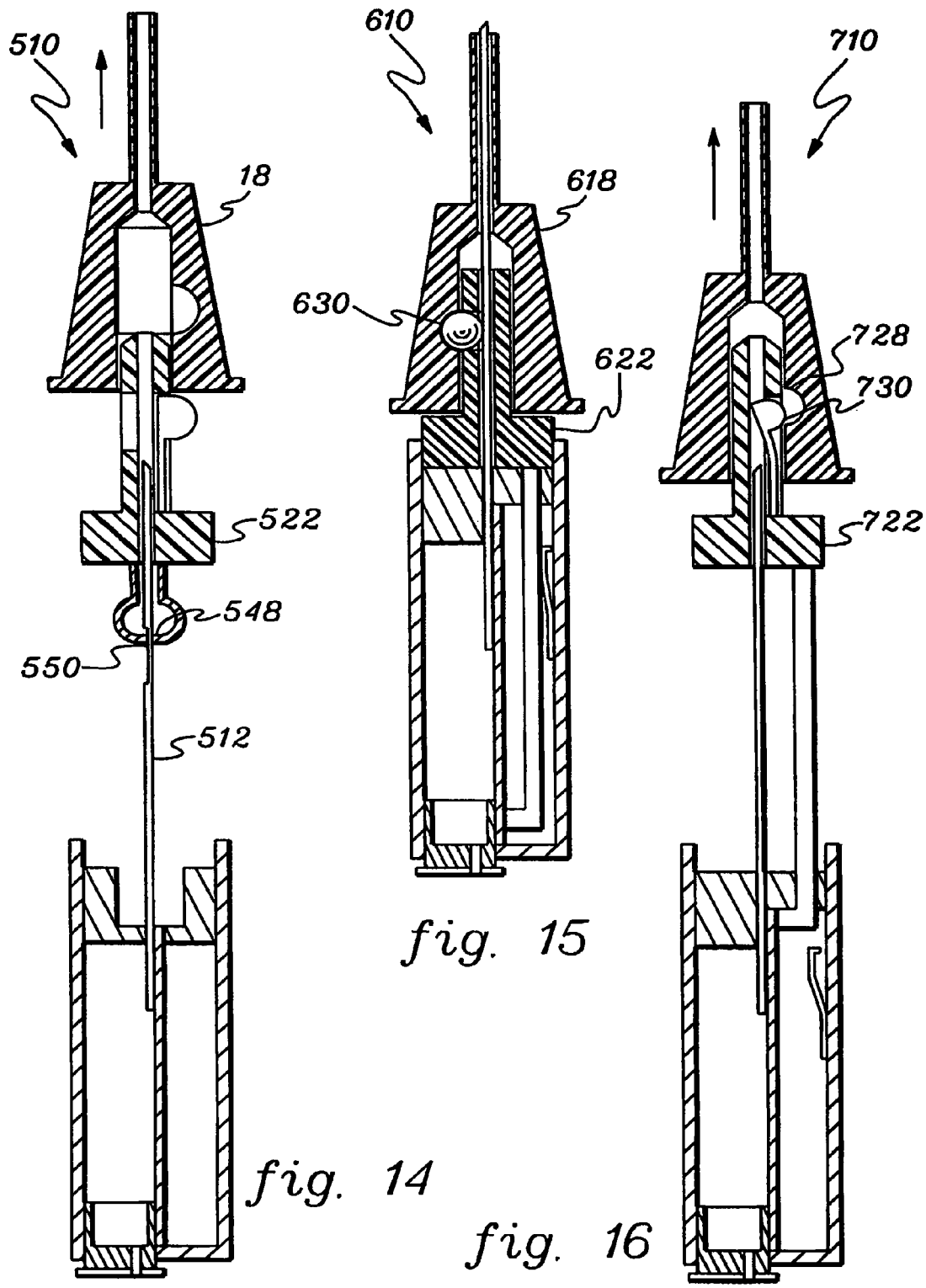

SAFETY INTRAVENOUS CATHETER ASSEMBLY

RELATED APPLICATIONS

This application is a continuation of U.S. patent application Ser. No. 10/961,832, filed on Oct. 8, 2004, which issued as U.S. Pat. No. 7,569,033 on Aug. 4, 2009, which is a continuation of international application PCT/US03/10756 filed on Apr. 9, 2003 and published, as international publication number WO 03/086499 on Oct. 23, 2003, and claims priority from and is a continuation of U.S. patent application Ser. No. 10/120,005 filed on Apr. 10, 2002, which issued as U.S. Pat. No. 6,689,102 on Feb. 10, 2004, which is a continuation-in-part of U.S. patent application Ser. No. 09/840,699, filed Apr. 23, 2001, which issued as U.S. Pat. No. 6,695,814 on Feb. 24, 2004, which is a continuation of U.S. patent application Ser. No. 09/127,374, filed Jul. 31, 1998, which issued as U.S. Pat. No. 6,221,047 on Apr. 24, 2001, the entirety of these patents are incorporated herein by reference.

TECHNICAL FIELD

This invention relates generally to catheter devices. More particularly, the invention relates to safety catheter devices having needlestick protection features.

BACKGROUND ART

Intravenous (IV) catheters are medical devices used to obtain continuous vascular access in patients. Such a device generally consists of a hollow-bore needle stylet and an over-the-needle plastic type material catheter used to access the lumen of a blood vessel in a patient. The IV catheter is advanced into the vessel and is used for administering intravenous fluids, medications or blood products, Since the IV catheter is placed percutaneously, the hollow-bore needle stylet becomes blood contaminated and, when the blood vessel lumen is accessed, the needle-stylet becomes blood-filled.

Needlestick injuries from IV catheter stylets are in the high-risk category for potential transmission of bloodborne pathogens to the injured health care worker, since they are hollow-bore needles which are usually filled with undiluted blood. The bloodborne pathogens of greatest concern include human immunodeficiency virus (HIV), the etiologic agent of the acquired immunodeficiency syndrome (AIDS), hepatitis B virus and hepatitis C virus.

There is therefore a need for safety intravenous catheters.

SUMMARY OF THE INVENTION

The present invention provides, in a first aspect, a safety intravenous catheter assembly having a needle, a catheter hub having an axial bore extending through the catheter hub and a notch extending outwardly in the axial bore, a needle cover, and a notch clip connected to the needle cover. The notch clip is positionable to engage the notch of the catheter hub and lock the catheter hub to the needle cover when the notch clip is inserted in the axial bore and a tip of the needle is inserted at least adjacent or past a distal portion of the notch clip, and positionable to disengage the notch when a tip of the needle is located prior to the distal portion of the notch clip to unlock the catheter hub from the needle cover. The notch clip is maintainable adjacent the needle throughout a range of positions from being in forceful contact with the needle to being generally spaced from the needle when the tip of the needle is inserted at least adjacent or past a distal portion of the notch clip, and maintainable adjacent the catheter hub throughout a range of positions from being in forceful contact with the catheter hub to being generally spaced from the catheter hub when the tip of the needle is inserted at least adjacent or past a distal portion of the notch clip. The notch clip and the needle are movable in a near frictionless relationship relative to one another when the notch clip is inserted past a distal portion of the notch clip.

The present invention provides, in a second aspect, a method for using a safety intravenous catheter assembly which includes inserting a needle through a needle cover and past a notch clip disposed in a catheter hub having an axial bore extending through the catheter hub and a notch extending outwardly in the axial bore to lock the catheter hub to the needle cover, selectively maintaining the notch clip adjacent the needle throughout a range of positions from being in forceful contact with the needle to being generally spaced from the needle, selectively maintaining the notch clip adjacent the catheter hub throughout a range of positions from being in forceful contact with the catheter hub to being generally spaced from the catheter hub, and moving the needle relative to the notch clip in a near frictionless relationship.

The present invention provides, in a third aspect, a safety intravenous catheter assembly having a needle, a catheter hub having an axial bore extending through the catheter hub, a needle cover, and means for selectively maintaining a notch clip adjacent the needle throughout a range of positions from being in forceful contact with the needle to being generally spaced from the needle and the notch clip adjacent the catheter hub throughout a range of positions from being in forceful contact with the catheter hub to being generally spaced from the catheter hub to lock the catheter hub to the needle cover while being operable to move the needle relative to the notch clip in a near frictionless relationship.

BRIEF DESCRIPTION OF THE DRAWINGS

The subject matter which is regarded as the invention is particularly pointed out and distinctly claimed in the claims at the conclusion of the specification. The features and advantages of the invention will be apparent from the following detailed description taken in conjunction with the accompanying drawings, which drawings illustrate several embodiments of the invention.

FIG. 3 is a cross-sectional side view of the assembly of FIG. 1 just prior to insertion of the needle into the needle cover and the stop bar into the needle case.

FIG. 4 is a cross-sectional side view of the assembly of FIG. 1 during insertion of the needle into the needle cover and the stop bar into the needle case.

FIG. 5 is a cross-sectional side view of the assembly of FIG. 1 with the needle fully inserted into the needle cover and the stop bar fully inserted into the needle case, and ready for insertion into a patient.

FIG. 6 is a cross-sectional side view of the assembly of FIG. 1 with the needle being withdrawn from the distal end of the needle cover, with the needle tip adjacent to the upper distal portion of the notch clip, and with the stop bar locked into the needle case by a detent.

FIG. 7 is a cross-sectional side view of the assembly of FIG. 1 with the needle being withdrawn from the upper distal portion of the notch clip, with the stop bar's L-shaped end abutting the end of the needle case, and with the catheter hub disengaging from the needle cover as the notch clip flexes inward.

FIG. 8 is a cross-sectional side view of the assembly of FIG. 1 with the catheter hub being fully disengaged from the needle cover and with the stop bar in a stopped position within the needle case thereby maintaining a tip of the needle within the needle cover.

FIG. 14 is a cross-sectional side view of another embodiment of a safety intravenous catheter assembly in accordance with the present invention, showing a ring-like stop of a needle cover engaging a stop notch of a needle for limiting withdrawal of the needle from the needle cover and where a catheter hub is disengaged from the needle cover.

FIG. 15 is a cross-sectional side view of another embodiment of a safety intravenous catheter assembly in accordance with the present invention, showing a ball bearing type of notch clip and with a needle fully inserted into a needle cover and a stop bar fully inserted into a needle case.

FIG. 16 is a cross-sectional side view of yet another embodiment of a safety intravenous catheter assembly in accordance with the present invention which is similar to the assembly of FIG. 1, except with the elimination of a notch in the needle cover.

DETAILED DESCRIPTION OF THE INVENTION

Figure 1:
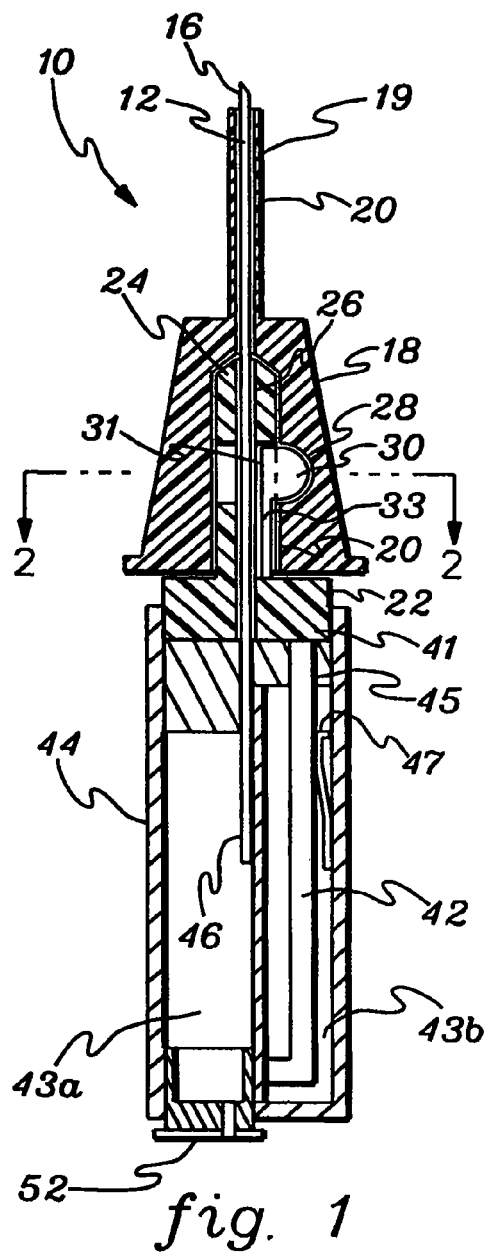
FIG. 1 is a partial cross-sectional side view of one embodiment of a safety intravenous catheter assembly in accordance with the present invention.

FIG. 1 illustrates a safety intravenous catheter assembly 10 in accordance with the present invention for use with a needle 12. Generally, safety intravenous catheter assembly 10 includes a catheter hub 18, a catheter cannula 19, a needle cover 22, a stop bar 42, and a needle case 44. The various embodiments of the present invention, as described in greater detail below, result in the safety intravenous catheter assemblies which after inserting the catheter cannula into a patient and removing the needle from the catheter cannula and catheter hub, automatically provides a non-removable protective cover over a tip of the needle thereby reducing the risk of needlestick injuries to health workers.

Safety intravenous catheter assembly 10 is configured so that catheter hub 18 is inhibited from rotating relative to needle cover 22. In the embodiment shown in FIGS. 1-8, the fixedly connected catheter hub 18 and needle cover 22 does not rotate around needle 12. In another aspect of the present invention, as explained in greater detail below in connection with FIGS. 9-13, a fixedly connected catheter hub and needle cover may, however, be made to rotate around the needle.

With reference again to FIG. 1, catheter cannula 19 is attached to catheter hub 18 and includes a first axial bore 20 extending through catheter cannula 19 and catheter hub 18. Needle cover 22 has a first upper end 24 insertable in axial bore 20 of catheter hub 18. A second axial bore 26 extends through needle cover 22 and may be co-axial with axial bore 20 when assembled.

The components of the assembly may be constructed from materials similar to those for pre-existing IV catheters and related parts. For example, sterile grade rigid plastic can be used to form catheter hub 18, needle cover 22, stop bar 42 and needle case 44. Stop bar 42 may alternatively be sterile grade stainless steel. Needle 12 may comprise a sterile grade stainless steel.

Figure 2:
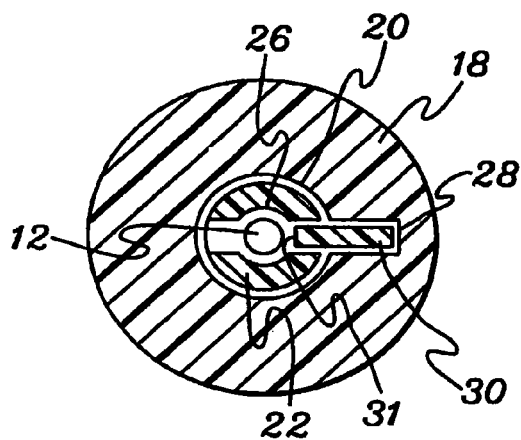
FIG. 2 is an enlarged sectional view taken along line 2-2 in FIG. 1.

With reference to FIGS. 1 and 2, catheter hub 18 includes a notch 28 extending outwardly from axial bore 20 of catheter hub 18. A notch clip 30 is joined via a resilient arm 33 with needle cover 22 and positionable to engage notch 28 of catheter hub 18. This enables catheter hub 18 to be fixedly connected so that catheter hub 18 does not rotate relative needle cover 22 when the two are fully engaged.

An inner surface of notch clip 30 may be substantially parallel to second axial bore 26. Notch clip 30 in a rest position may be spaced from or in a non-forceful contact with needle 12, so that notch clip 30 at most rests against needle 12 as in side-by-side non-forceful contact. For example, an annular space 31 may be provided adjacent notch clip 30 and second axial bore 26. In addition, appropriately sizing the notch clip may result in the notch clip being spaced from the needle and spaced from the notch in the catheter hub.

In this configuration, the assembly reduces and limits the frictional drag between notch clip 30 and needle 12 when needle 12 is inserted into and withdrawn from needle cover 22. The notch clip and the needle cover may be monolithic and integrally formed as one-piece. Alternatively, the notch clip could be an independent piece configured for a snap fit or bonded or glued relationship with the needle cover. As described above, the radially inward side or inner surface of the notch clip may be in or adjacent to the annular space 31, e.g., not continuously contacting, and at most co-planar with a second surface 27 (FIG. 3) defined by an outer circumference of the second axial bore when the notch clip is at rest.

Notch clip 30 and arm 33 are preferably made of a resilient type material having a characteristic which enables it to flex radially inward with minimal force. This force is provided by notch 28 and a bottom portion of the catheter hub 18 as the catheter hub disengages from the needle cover. This disengagement preferably only occurs when a needle tip 16 (FIG. 1) is located below or away from an upper distal portion of the notch clip, i.e., when removing the protected needle from the catheter hub, as explained in greater detail below.

With reference particularly to FIG. 1, embodiments of the present invention may include additional safety features such as a stop assembly joined with a second end 41 of needle cover 22. The joined relationship may be obtained by forming integral or a conventional bonding or gluing process, or a snap-fit relation. The stop assembly serves to limit withdrawal of the needle from the needle cover by maintaining the tip of the needle inside second axial bore 26 of needle cover 22.

For example, the stop assembly may comprise stop bar 42 joined with the needle cover at the second end. In this embodiment the stop assembly further includes needle case 44 joined with the needle at a lower end 46 of the needle, such as by a conventional forming, bonding or gluing process. As should be apparent, the lower end of the needle is in fluid flow communication with the needle case via a chamber 43a. The stop bar communicates with the needle case via an opening 45 in a second chamber 43b. The stop bar 42, needle case 44, and a detent 47 are designed so that sliding movement of the stop bar has minimal frictional drag (FIGS. 4 and 5 as described in greater detail below). The stop bar and detent 47 may be of any design to stop the bar at the desired length of extension. The stop bar may also be designed to extend telescopically and then lock, which would decrease the needle case length.

Assembly and use of safety intravenous catheter assembly 10 is illustrated in FIGS. 3-8. As will become apparent for the following description, the relationship between the notch and the notch clip, and the stop assembly, contributes to several of the features and advantages of the present invention.

With reference to FIG. 3, initially first upper end 24 of needle cover is inserted in axial bore 20 of catheter hub 18 and the upper distal portion of notch clip is aligned to slip into notch 28 when needle cover is loaded into catheter hub 18. This moves the upper distal portion of the notch clip completely out of the second axial bore which permits preferred unrestricted movement of needle 12 into the second axial bore, thus facilitating easy assembly of the device.

Next, with reference to FIG. 4, stop bar 42 of assembly 10 is inserted into needle case 44 and needle 12 is aligned with second axial bore 26. When the needle is inserted in the second axial bore at least adjacent or past an upper distal portion of the notch clip, the notch clip can engage the side of the needle and notch 28 and lock the catheter hub in engagement with the needle cover. FIG. 5 illustrates safety intravenous catheter assembly 10 in the configuration for insertion into a patient. The needle maintains the notch clip in the notch and automatically inhibits the catheter hub from disengaging from the needle cover prematurely.

Any of several approaches could be used for assembly such as where the needle case is intact and fully enclosed or by having a side opening which is later covered and sealed closed. With reference again to FIG. 3, if the needle case is fully enclosed in final form and, for example, opening 45 is slot shaped, the stop bar can be rotated ninety degrees and inserted into the needle case and rotated back ninety degrees. The stop bar then passes by resilient detent 47, by having detent 47 retracted radially outward to permit the stop bar to be inserted. For example, this radial retraction can be accomplished via a hook externally or other device via a small opening in the outside wall of chamber 43b or other conventional means.

The process of catheter insertion of assembly 10 in a patient is illustrated in FIGS. 5-8. Initially, with reference to FIG. 5, the process involves placing needle tip 16 into a vessel lumen. After placing needle tip 16 into the vessel lumen, the user holds needle case 44 stationary (which maintains needle 12 stationary) and advances catheter cannula 19 into the vessel lumen until catheter hub 18 abuts the skin. Then needle case 44 is withdrawn to completely withdraw needle 12 from catheter cannula 19 and partially withdraw needle 12 from catheter hub 18.

As shown in FIG. 6, as stop bar 42 is withdrawn from the needle case, detent 47 continues to be forced to the right until eventually, the L-shaped portion of the stop bar passes beyond the distal aspect of detent 47 and the detent can spring underneath the L-shaped portion. This action serves to stop the re-insertion of the stop bar into the second chamber 43b. At this position needle tip 16 is adjacent to the upper distal portion of notch clip 30.

The stop bar is withdrawn a small amount more from the needle case, as shown in FIG. 7, so that the needle tip is located prior to the upper distal portion of the notch clip thereby allowing the catheter hub to be disengaged from the needle cover. This preferred small additional movement of the stop bar ensures that the catheter hub does not disengage from the needle cover until the stop bar's L-shaped end is locked above detent 47 and the needle tip is thereby locked inside the needle cover. Thereafter, as shown in FIG. 8, the catheter hub 18 can be fully disengaged from the needle cover 22.

Figure 18:
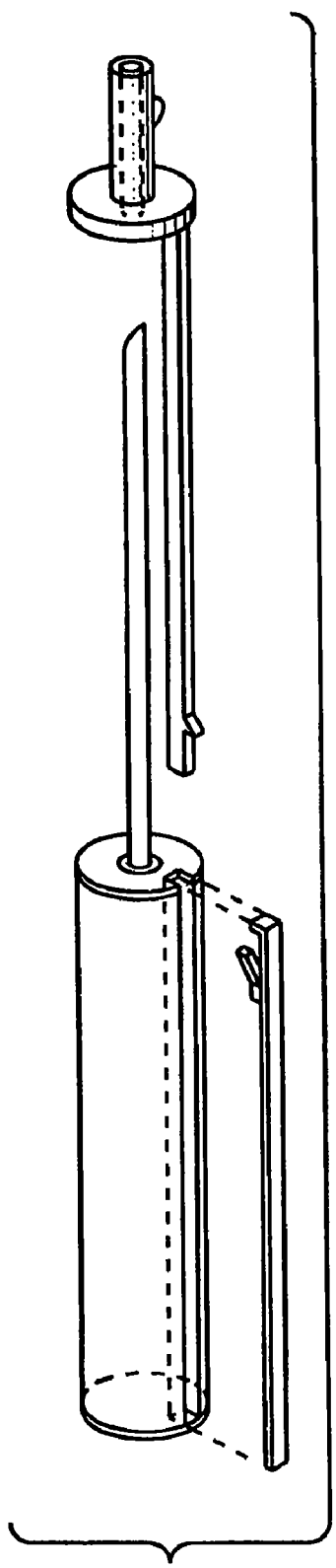
FIG. 18 is an exploded perspective view of another embodiment of a safety intravenous catheter assembly in accordance with the present invention.
Figure 19:
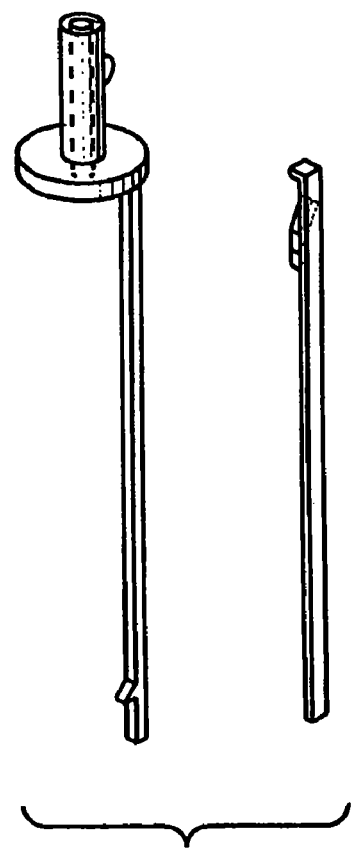
FIG. 19 is another embodiment of a needle cover and a stop assembly in accordance with the present invention for use in a safety intravenous catheter assembly.

Any alternative mechanism to the detent can be used as long as it functions to lock into the final position, as described above, the L-shaped or other shaped end of the stop bar and such that there is preferably a minimum of frictional drag during catheter insertion. For example, FIGS. 18 and 19 illustrate alternative embodiments of the configurations for the needle cover and the stop mechanism.

Another aspect of the present invention is illustrated in FIGS. 9-13, in which means are provided for rotatably attaching at least one of the needle case and the stop assembly in relation to the needle cover so that the needle cover and the catheter hub as a unit is rotatable around the axis of the needle particularly when inserting the cannula into the patient.

Figure 9:
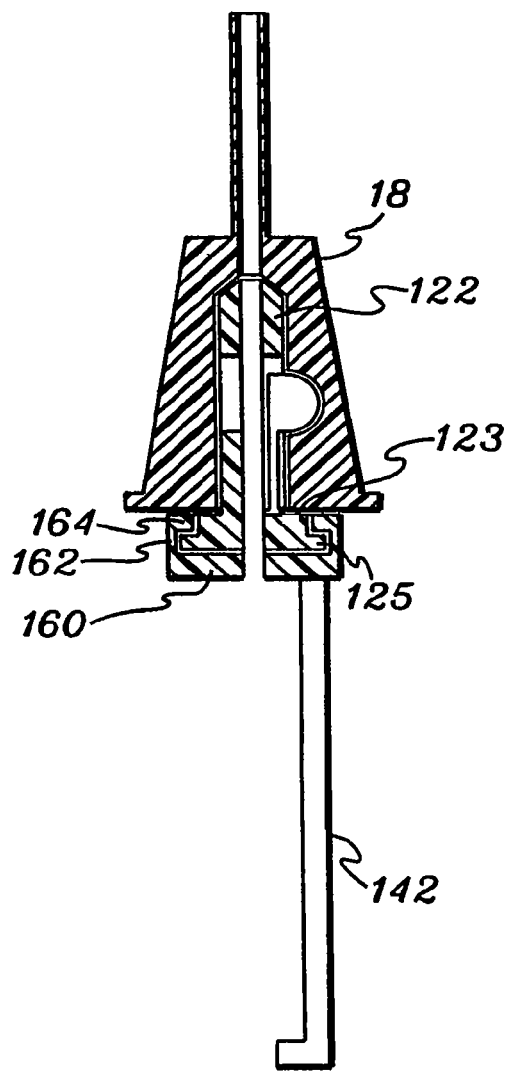
FIG. 9 is a cross-sectional side view of another embodiment of a needle cover and a stop bar in accordance with the present invention which allows the catheter hub and needle cover together as a unit to rotate around the needle when inserting the catheter cannula into a patient.

For example, with reference to FIG. 9, therein illustrated are catheter hub 18 and a needle cover 122. Needle cover 122 includes a disk-shaped bottom portion 123 having an outwardly-extending flange 125. The stop assembly includes a stop bar 142 having a disk-shaped member 160 having an upwardly-extending portion 162 with an inwardly-extending flange 164 which is attachable to outwardly-extending flange 125 of needle cover 122, for example, in a snap-fit manner. In this configuration, the bottom portion of the needle cover and the disk-shaped member of the stop bar may be suitably sized to allow the bottom portion of the needle cover to rotate within the disk-shaped member of the stop bar.

Figure 10:
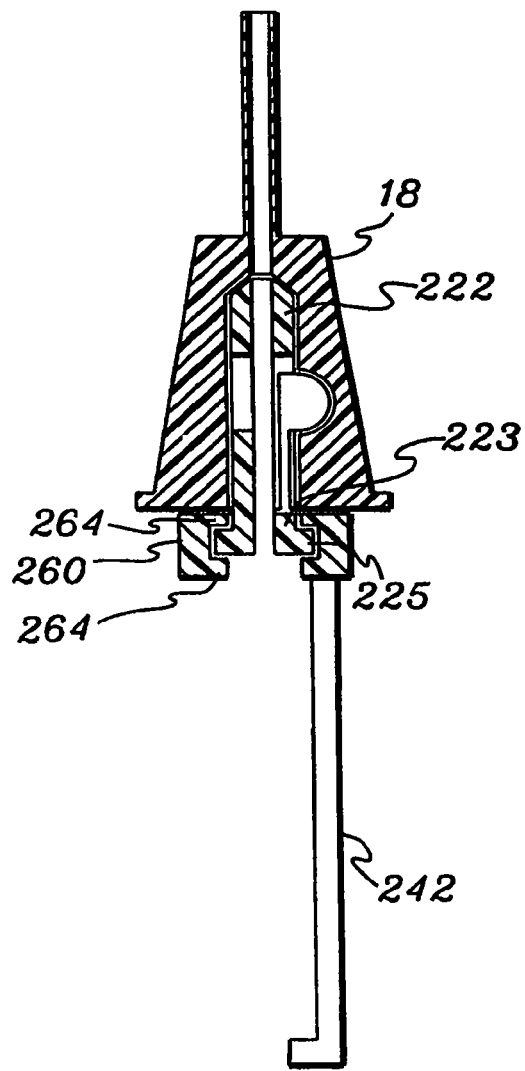
FIG. 10 is a cross-sectional side view of another embodiment of a needle cover and a stop bar in accordance with the present invention which allows the catheter hub and needle cover together as a unit to rotate around the needle when inserting the catheter cannula into a patient.

With reference to FIG. 10, therein illustrated are catheter hub 18 and a needle cover 222. Needle cover 222 includes a bottom portion 223 having an outwardly-extending flange 225. The stop assembly includes a stop bar 242 having a ring-shaped member 260 having a pair of spaced-apart inwardly-extending flanges 264 for attaching to outwardly-extending flange 225 of bottom portion 223, for example, in a snap-fit manner. The bottom portion of the needle cover and the ring-shaped member of the stop bar may be suitably sized to allow the bottom portion of the needle cover to rotate within the ring-shaped member of the stop bar.

Figure 11:
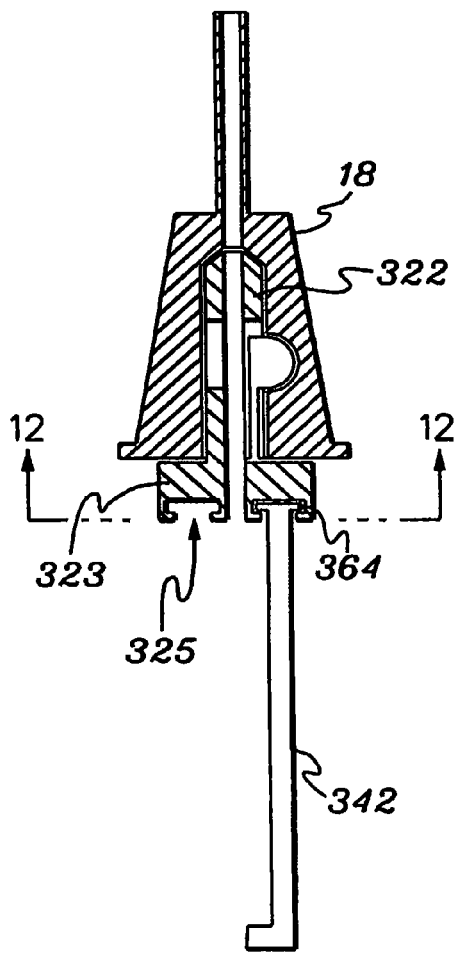
FIG. 11 is a cross-sectional side view of another embodiment of a needle cover and a stop bar in accordance with the present invention which allows the catheter hub and needle cover together as a unit to rotate around the needle when inserting the catheter cannula into a patient.
Figure 12:
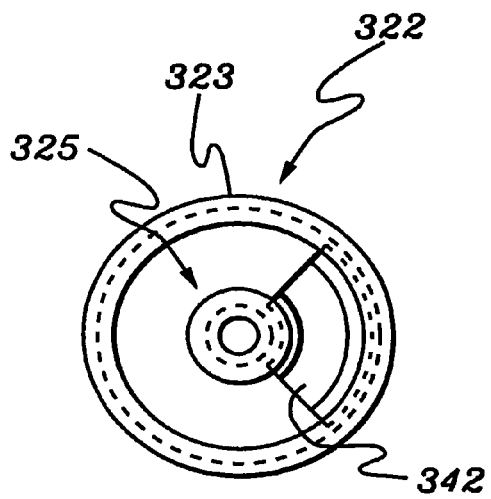
FIG. 12 is an enlarged sectional view taken along line 12-12 in FIG. 11.

FIGS. 11 and 12 illustrate another embodiment of a catheter hub 18 (FIG. 11) and a needle cover 322. Needle cover 322 includes a bottom portion 323 having a groove 325. The stop assembly includes a stop bar 342 having an upper end having a pair of outwardly-extending flanges 364 (FIG. 11) attachable to and movable within groove 325. Flanges 364 may be received in groove 325 in a snap-fit manner. The groove in the bottom the needle cover and the upper end of the stop bar may be suitably sized to allow the stop bar to easily rotate within the groove.

Figure 13:
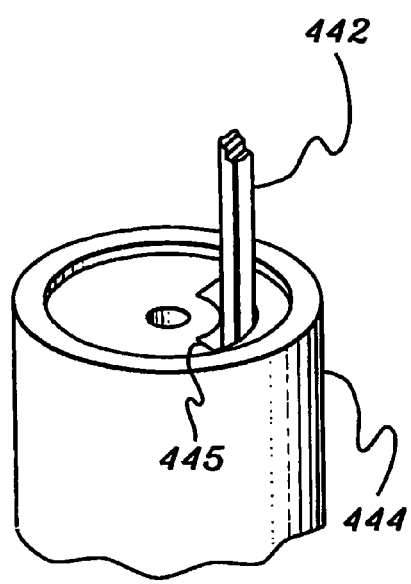
FIG. 13 is a perspective view of another embodiment of a needle case in accordance with the present invention which allows a catheter hub and a needle cover together as a unit (not shown) to rotate around the needle when inserting the catheter cannula into a patient.

FIG. 13 illustrates a needle case 444 in which an opening 445 has an arcuate configuration to allow a stop bar 442 to rotate around the axis of the needle, e.g., an amount less than 360-degrees. From the present description, It will be appreciated by those skilled in the art that the opening may be an annular opening, for example, the center portion of the needle case may be attached to the bottom of the needle case, thereby permitting a 360-degree rotation of the stop bar around the axis of the needle.

From the present description, it will be appreciated by those skilled in the art that the various safety intravenous catheter assemblies described above may be configured for 360-degree rotation of the catheter hub and needle cover as a unit around the axis of the needle, or configured for less than 360-degree rotation.

The needle cover and notch clip's design provide selective sliding engagement with the side of the needle such that there is minimal, and preferably no, frictional drag so that catheter hub and needle cover as a unit may easily rotate around the needle axis, and also, so that the catheter hub and needle cover combined can easily move distally towards the needle tip during IV catheter insertion.

In another embodiment as shown in FIG. 14, a safety intravenous catheter assembly 510 in accordance with the present invention may include the stop member comprising a ring-like stop 548 joined to the lower end of a needle cover 522, and a needle 512 having a stop notch 550 located in the side of the needle. In operation, as the needle is withdrawn from the needle cover, ring-like stop 548 engages stop notch 550 thereby maintaining the tip of the needle inside needle cover 522. Then, the catheter hub 18 can be removed in a similar fashion as described previously. In this embodiment, the ring-like stop 548 is preferably constructed of a resilient material that is sized to automatically and continuously engage the circumference of needle 512. When being assembled, the ring-like stop can be temporarily relaxed to enable insertion of the needle into needle cover 522 and passing stop notch 550 past ring-like stop 548.

Other aspects of the invention may concern the notch clip. For example, as shown in FIGS. 1-11, the notch clip is configured as a P-shaped member. In another embodiment, as shown in FIG. 15, a safety intravenous catheter assembly 610 in accordance with the present invention may include a notch clip comprising a ball bearing 630 which engages a concave notch disposed in catheter hub 618 to releasably lock a needle cover 622 to catheter hub 618.

FIG. 16 illustrates still another embodiment a safety intravenous catheter assembly 710 in accordance with the present invention. When the needle diameter is sufficiently large, a needle cover 722 may not require a notch disposed opposite a notch clip 730 if the second axial bore is large enough to ensure the notch clip distal portion completely disengages notch 728 during withdrawal of the needle cover from the catheter hub.

As understood herein, withdrawn, withdrawal or withdrawing means any movement of one member away from another member in the range from partial withdrawal (at least some portion of the respective members are still in communication with each other) to complete withdrawal (no portion of the respective members are in communication with each other). With reference again to FIGS. 5-8, generally as the catheter cannula is advanced into a vessel and the needle is withdrawn from the second axial bore, the user can, if desired, hold or engage the exposed needle cover portion adjacent the stop bar.

Figure 17:
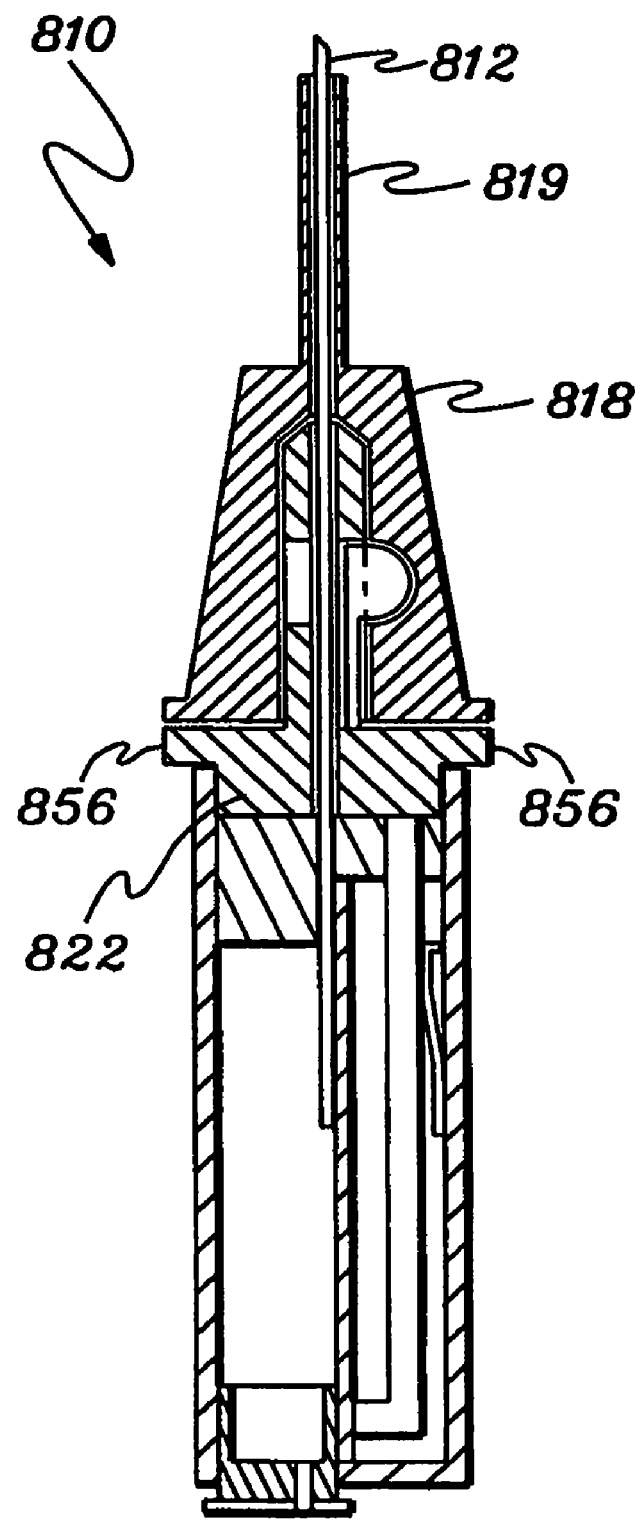
FIG. 17 is a cross-sectional side view of yet another embodiment of a safety intravenous catheter assembly in accordance with the present invention which is similar to the assembly of FIG. 1, except including an optional needle cover finger rest.

FIG. 17 illustrates another embodiment of a safety intravenous catheter assembly 810 in accordance with the present invention. For example, when advancing a catheter cannula 819 into a vessel and withdrawing a needle 812 from a catheter hub 818 which is still fully engaged with a needle cover 822, needle cover 822 may be provided a finger rest 856. In this way, one can advance the catheter cannula and withdraw the needle without pushing directly with the catheter hub by instead pushing the catheter hub via the needle cover and most preferably the finger rest, thereby enabling cannula advancement and withdrawal of the needle with minimal, and preferably no, friction between the needle and the notch clip. Finger rest 856 may comprise an annular ring or one or more protrusions extending from the needle cover. Also, it is preferred that finger rest 856 extend no further than the outer circumference of the adjacent portion of the catheter hub 818, though a longer extension may be desired by some users. Alternatively, instead of using finger rest 856, the user can advance the cannula and withdraw the needle by pushing directly with catheter hub 818.

Various additional uses can be made with the safety intravenous catheter assemblies. For example, with reference again to FIG. 1, to assist in the insertion of the cannula into a blood vessel or body cavity, a flexible guide wire (not shown) can be inserted via an opening 52 in the chamber 43a and advanced into the first end 46 of the needle and made to exit tip 16 (i.e., Seldinger wire technique for vascular access). In this regard a minor modification (not shown) of the chamber's internal shape would facilitate easy access of a flexible guide wire into needle end 46. Alternatively, a syringe (not shown) can be attached to chamber 43a via opening 52, for communicating a fluid to or from the chamber 43a. Although not shown, opening 52 may be located in the center of the proximal end of the needle case, which is accomplished by making conventional modifications of the needle case.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A method for using a catheter assembly, the method comprising:
providing a catheter assembly comprising: a needle;
a needle cover having a first passageway extending therethrough for receiving said needle;
a catheter hub having a second passageway extending therethrough and having a notch having a longitudinal length;
a notch clip positionable in said notch of said catheter hub; and said notch clip cooperating with said needle to lock said catheter hub to said needle cover when said needle cover is disposed in said catheter hub and said needle is disposed in said needle cover distal to said notch clip with said notch clip comprising an inner longitudinally-extending surface spaced-apart from and parallel to said needle along a longitudinal length of said notch clip that is substantially equal to and aligned with said longitudinal length of said notch; and when said needle cover is completely removed from said catheter hub said notch clip is not in contact with said needle; and moving the needle relative to the notch clip in at least one of a frictionless and near frictionless relationship.

2. The method of claim 1 wherein said needle comprises a constant cross-sectional size along an entire length of said needle and a pointed tip at one end.

3. The method of claim 1 wherein said notch clip comprises a resilient P-shaped member.

4. The method of claim 1 wherein said notch clip comprises a normal non-biased position when said needle cover is disposed in said catheter hub and said needle is disposed in said needle cover.

5. A catheter assembly comprising:
a needle;
a catheter hub having a second passageway extending therethrough and a notch therein;
a needle cover having a notch clip and a first passageway extending therethrough for receiving said needle, said notch clip comprising a resilient material offering resistance to said notch clip from obstructing said first passageway, at least a portion of an inner surface of said notch clip positioned away from said needle when said needle is disposed in said needle cover, and when said needle cover is completely removed from said catheter hub said notch clip is not in contact with said needle;
said notch clip and the needle cooperating to engage said notch of said catheter hub and lock said catheter hub to said needle cover when said notch clip is inserted in said catheter hub and a tip of said needle is inserted at least adjacent or past a distal portion of said notch clip;
said notch clip positionable to disengage said notch when a tip of said needle is located prior to said distal portion of said notch clip to unlock said catheter hub from said needle cover; and
said notch clip and said needle being movable in at least one of a frictionless and near frictionless relationship relative to one another when said first end of said needle cover is inserted in said catheter hub and the tip of the needle is inserted at least adjacent to or above said notch clip.

6. The assembly of claim 5 wherein said catheter hub and said notch clip are movable in at least one of a frictionless and near frictionless relationship relative to one another.

7. The assembly of claim 5 wherein a portion of said needle cover is receivable within said catheter hub.

8. The assembly of claim 5 wherein said needle comprises a constant cross-sectional size along an entire length of said needle and a pointed tip at one end.

9. A method for using a catheter assembly, the method comprising: providing a needle, a needle cover having a notch clip and a first passageway extending therethrough for receiving said needle, and a catheter hub having a second passageway extending therethrough and a notch therein, said notch clip comprising a resilient material offering resistance to said notch clip from obstructing said first passageway, at least a portion of an inner surface of said notch clip positioned away from said needle when said needle is disposed in said needle cover, and when said needle cover is completely removed from said catheter hub said notch clip is not in contact with said needle, and wherein said notch clip and said needle cooperate to lock said needle cover to said catheter hub when said notch clip is inserted in said catheter hub and a tip of said needle is inserted at least adjacent or past a distal portion of said notch clip; and
moving the needle relative to the notch clip in at least one of a frictionless and near frictionless relationship.

10. The method of claim 9 further comprising locking the needle in the needle cover upon withdrawing the needle past the notch clip.

11. The method of claim 9 wherein said needle comprises a constant cross-sectional size along an entire length of said needle and a pointed tip at one end.

* * * * *